(12) United States Patent
Stephenson

(10) Patent No.: US 8,863,747 B1
(45) Date of Patent: Oct. 21, 2014

(54) TRIPLE ACCESS DRAPE AND METHOD OF USING SAME

(71) Applicant: Welmed, Inc., Chicago, IL (US)

(72) Inventor: Deborah Stephenson, Whiteville, NC (US)

(73) Assignee: Welmed, Inc., Chicago, IL (US)

( * ) Notice: Subject to any disclaimer, the term of this patent is extended or adjusted under 35 U.S.C. 154(b) by 0 days.

(21) Appl. No.: 14/039,506

(22) Filed: Sep. 27, 2013

(51) Int. Cl.
- A61B 19/08 (2006.01)
- A61B 19/00 (2006.01)
- A61B 19/12 (2006.01)

(52) U.S. Cl.
CPC ..................... *A61B 19/12* (2013.01)
USPC ........................... 128/854; 128/849

(58) Field of Classification Search
USPC ......... 128/849–856, DIG. 24; 383/33, 63, 65; 604/357
See application file for complete search history.

(56) References Cited

U.S. PATENT DOCUMENTS

| | | | |
|---|---|---|---|
| 3,799,161 A | 3/1974 | Collins | |
| 4,119,093 A * | 10/1978 | Goodman | 128/856 |
| 5,140,996 A * | 8/1992 | Sommers et al. | 128/849 |
| 5,640,975 A | 6/1997 | Diao | |
| 6,199,553 B1 * | 3/2001 | Hafer et al. | 128/849 |
| 6,298,855 B1 | 10/2001 | Baird | |
| 6,843,252 B2 | 1/2005 | Harrison et al. | |
| 7,114,500 B2 | 10/2006 | Bonutti | |
| 7,958,894 B2 | 6/2011 | Katoh et al. | |
| 8,079,365 B2 * | 12/2011 | Block et al. | 128/853 |
| 8,100,130 B2 | 1/2012 | Allen et al. | |
| 8,322,345 B2 | 12/2012 | West | |
| 8,371,306 B2 | 2/2013 | Haines et al. | |
| 2008/0283064 A1 | 11/2008 | Block et al. | |
| 2012/0298115 A1 * | 11/2012 | Haines et al. | 128/852 |
| 2013/0125901 A1 * | 5/2013 | Pitaoulis | 128/851 |

* cited by examiner

*Primary Examiner* — Ophelia A Hawthorne
(74) *Attorney, Agent, or Firm* — Jerry R. Potts; James R. McDaniel

(57) ABSTRACT

A medical drape, including a main sheet having at least one opening for access to a patient's femoral artery, and at least one adjustable arm board cover substantially located at one end of the main sheet wherein the adjustable arm board cover includes at least one opening for access to the patient's brachial artery and at least one opening for access to the patient's radial artery.

18 Claims, 6 Drawing Sheets

TRIPLE ACCESS DRAPE AND METHOD OF USING SAME

FIELD OF THE INVENTION

This invention relates generally to medical drapes and more particularly to a drape that can be placed over a patient prior to a medical procedure such as surgery that provides access to the patient's brachial, radial and femoral arteries without having to reposition the drape and/or the patient.

BACKGROUND OF THE INVENTION

Prior to the present invention, as set forth in general terms above and more specifically below, it is known, to use medical drapes, some of which include openings or fenestrations. See for example, U.S. Pat. No. 8,371,306 to Haines, et al., U.S. Pat. No. 8,322,345 to West, U.S. Pat. No. 8,100,130 to Allen, et al., U.S. Pat. No. 7,958,894 to Katoh, et al., U.S. Pat. No. 7,114,500 to Bonutti, U.S. Pat. No. 6,843,252 to Harrison, et al., U.S. Pat. No. 6,298,855 to Baird, U.S. Pat. No. 5,640,975 to Diao, U.S. Pat. No. 3,799,161 to Collins, and U.S. Patent Application Publication No. 20080283064 to Block, et al. While the use of medical drapes having fenestrations may have been generally satisfactory, there is nevertheless a need for a triple access, full body drape having radial, brachial, femoral approach accesses with adjustable arm board covers and a clear anesthesia window.

It is a purpose of this invention to fulfill this and other needs in the art in a manner more apparent to the skilled artisan once given the following disclosure.

SUMMARY OF THE INVENTION

A feature of the present invention is a medical drape, including a main sheet having at least one opening for access to a patient's femoral artery, and at least one adjustable arm board cover substantially located at one end of the main sheet wherein the adjustable arm board cover includes at least one opening for access to the patient's brachial artery and at least one opening for access to the patient's radial artery.

Another feature of the present invention is the provision of a medical drape, wherein the main sheet further includes two openings.

Another feature of the present invention is the provision of a medical drape, wherein the main sheet further includes at least one adhesive ring located substantially over the at least one opening.

Another feature of the present invention is the provision of a medical drape, wherein the adhesive ring further includes an anesthesia window that is located substantially over the at least one opening.

Another feature of the present invention is the provision of a medical drape, wherein the main sheet further includes a protective panel located substantially over the adhesive ring.

Another feature of the present invention is the provision of a medical drape, wherein the adjustable arm board cover further includes two openings.

Another feature of the present invention is the provision of a medical drape, wherein the adjustable arm board cover further includes at least one adhesive ring located substantially over the at least one opening for access to the patient's brachial artery and at least one adhesive ring located substantially over the at least one opening for access to the patient's radial artery.

Another feature of the present invention is the provision of a medical drape, wherein the adhesive ring further includes an anesthesia window that is located substantially over the at least one opening for access to the patient's brachial artery and an anesthesia window that is located substantially over the at least one opening for access to the patient's radial artery.

Another feature of the present invention is the provision of a medical drape, wherein the adjustable arm board cover further includes a protective panel located substantially over the at least one adhesive ring located substantially over the at least one opening for access to the patient's brachial artery and a protective panel located substantially over the at least one adhesive ring located substantially over the at least one opening for access to the patient's radial artery.

Another feature of the present invention is the provision of a medical drape, wherein the medical drape further includes at least one drape fold operatively connected to the main sheet and the adjustable arm board cover.

Another feature of the present invention is the provision of a medical drape, wherein the main sheet and the adjustable arm board cover are constructed of any suitable fire retardant, chemical resistant, and biodegradable material.

Another feature of the present invention is the provision of a medical drape, wherein the drape fold is constructed of any suitable fire retardant, chemical resistant, and biodegradable material.

Another feature of the present invention is the provision of a medical drape, wherein the adhesive ring is constructed of any suitable adhesive incise material Another feature of the present invention is the provision of a medical drape, wherein the anesthesia window is constructed of clear polyethylene.

Another feature of the present invention is the provision of a medical drape, wherein the protective panel is constructed of any suitable fire retardant, chemical resistant, and biodegradable spunbond, meltblown, spunbond nonwoven (SMS) material.

A further feature of the present invention is the provision of a method of attached a triple access drape to a patient, wherein the method includes the steps of: placing the triple access drape substantially over the patient, wherein the triple access drape includes a main sheet having at least one opening for access to a patient's femoral artery, and at least one adjustable arm board cover substantially located at one end of the main sheet wherein the adjustable arm board cover includes at least one opening for access to the patient's brachial artery and at least one opening for access to the patient's radial artery; locating the at least one opening for access to a patient's femoral artery substantially over the patient's femoral artery; locating the at least one opening for access to the patient's brachial artery substantially over the patient's brachial artery; locating the at least one opening for access to the patient's radial artery substantially over the patient's radial artery; and securing the triple access drape at the at least one openings for access to a patient's femoral artery, brachial artery and radial artery.

Another feature of the present invention is the provision of a method of attached a triple access drape to a patient, wherein the method includes the step of lifting a protective panel located substantially over each of the at least one openings for access to the patient's femoral, brachial, and radial arteries to access the patient's femoral, brachial, and radial arteries.

A further feature of the present invention is the provision of a method of attached a triple access drape to a patient, wherein the method includes the step of inserting a medical device substantially through an anesthesia window located substantially under each of the protective panels.

A further feature of the present invention is the provision of a method of attached a triple access drape to a patient, wherein the method includes the step of using an adhesive ring to secure the triple access drape to the patient.

A yet further feature of the present invention is the provision of a medical drape, including a main sheet having at least one opening for access to a patient's femoral artery, at least one adjustable arm board cover substantially located at one end of the main sheet wherein the adjustable arm board cover includes at least one opening for access to the patient's brachial artery and at least one opening for access to the patients radial artery, and at least one drape fold operatively connected to the main sheet and the adjustable sheet extension.

The preferred medical drape, according to various embodiments of the present invention, offers the following advantages: ease of use; economy of design; the patient does not need to be re-draped in order to achieve access; and the adjustable arm board covers create a hinged design that allows access to the patient regardless of position.

BRIEF DESCRIPTION OF DRAWINGS

The above mentioned features and steps of the invention and the manner of attaining them will become apparent, and the invention itself will be best understood by reference to the following description of the embodiments of the invention in conjunction with the accompanying drawings, wherein like characters represent like parts throughout the several views and in which.

DETAILED DESCRIPTION OF PREFERRED EMBODIMENTS

Figure 1:
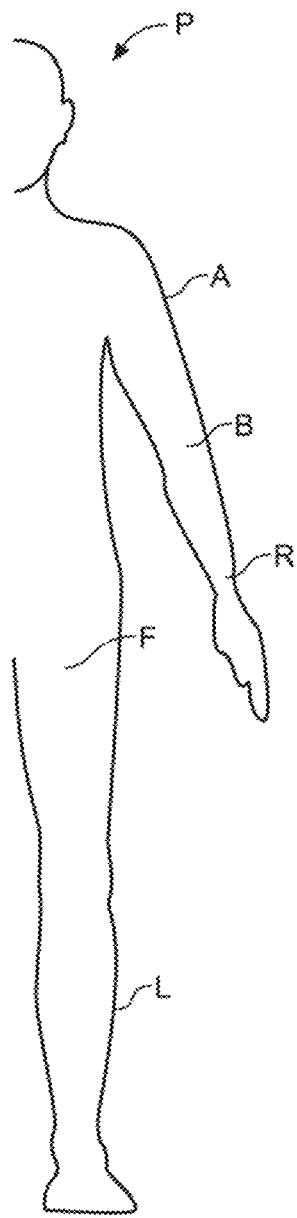
FIG. 1 is a schematic illustration of a left side of a human body, illustrating the locations of the femoral, brachial and radial arteries.

To provide some perspective that will be helpful in understanding and appreciating the inventive concepts of the present invention, it is well known that when medications are administered to a patient P, some of the most efficient locations to administer those medications are into the patient's femoral F, brachial B and/or radial R arteries. FIG. 1 schematically illustrates the common locations along the patient's P femoral F, brachial B and radial R arteries for administering the medications. As can be seen in FIG. 1, the femoral F artery is located in the patient's leg L. The brachial B and radial R arteries are located in the patient's arm A. Based upon the distances between the femoral F, brachial B and radial R arteries, it would be highly desirable to be able to access any or all of these arteries without having to adjust or move the patient P.

Referring now to the drawings and more particularly to FIGS. 2-7, there is illustrated a triple access drape 2, which is constructed in accordance with the present invention. As will be explained hereinafter in greater detail, the triple access drape 2 is constructed to be placed over a patient P (FIG. 1) prior to a medical procedure, such as a surgical procedure, such that the patient's femoral F, brachial B and radial R (FIG. 1) arteries can be easily accessed during the medical procedure without having to re-position the triple access drape 2. The advantages of triple access drape 2 are ease of use, economy of design, the patient does not need to be re-draped in order to achieve access, and the adjustable arm board covers create a hinged design that allows access to the patient regardless of patient position.

Figure 2:
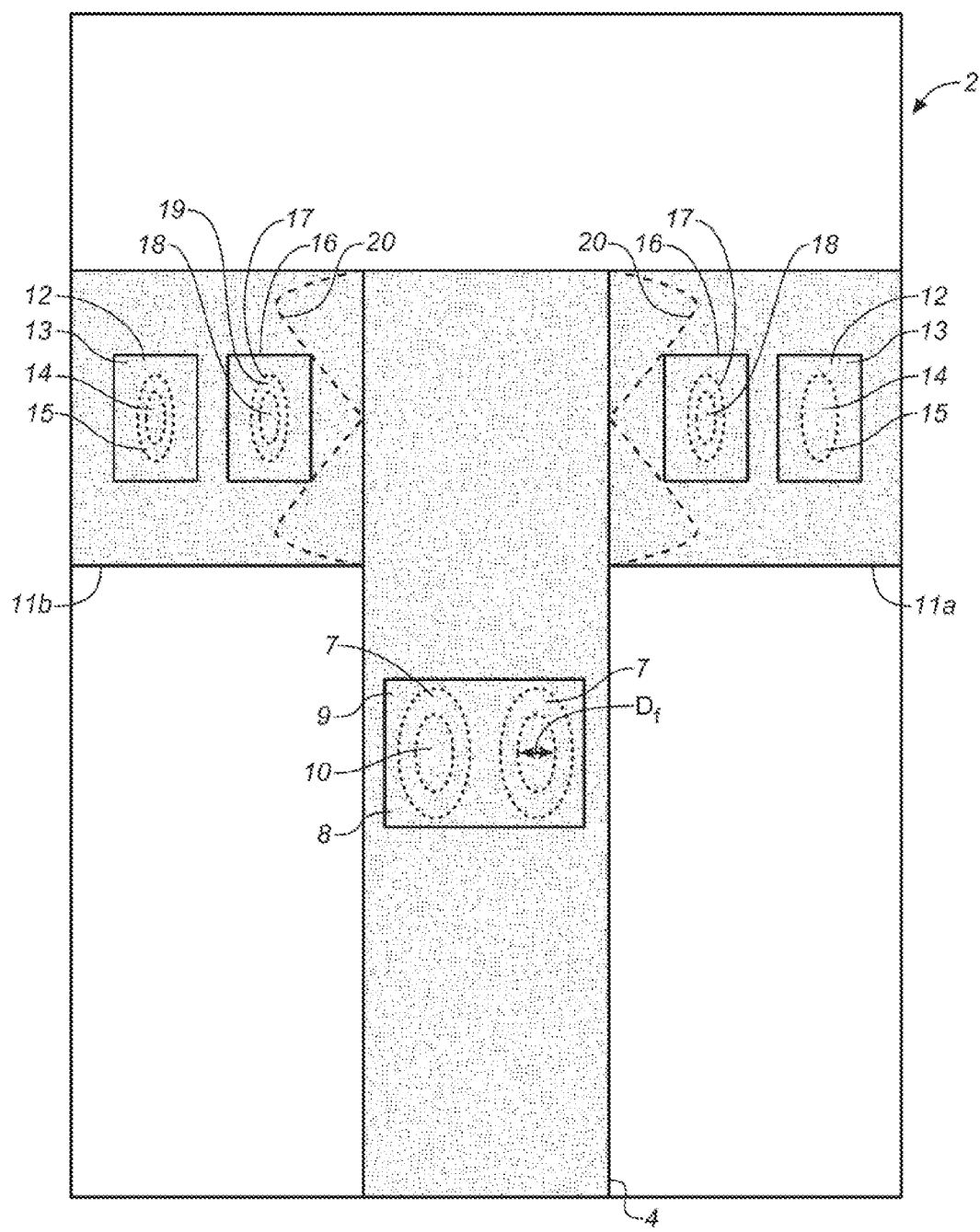
FIG. 2 is a top view of a triple access drape, constructed according to the present invention.

Considering now the triple access drape 2 in greater detail with reference to FIG. 2, the triple access drape 2 generally comprises a main body or longitudinal sheet 4 dimensioned to cover the torso of a patient from the neck to the ankles and a pair of arm or lateral adjustable arm board covers 11a and 11b dimensioned to cover the arms of a patient from the shoulder to about the midpoint of the lower arm. Main sheet 4 includes openings or fenestrations 10. Openings 10 can be utilized to access the patient's femoral F arteries in each of the patient's legs L (FIG. 1). Adjustable arm board covers 11a and 11b include openings 14 and 18. Openings 14 and 18 can be utilized to access the patient's radial R and brachial B arteries, respectively, in each of the patient's arms A (FIG. 1).

Positioned over opening 10 is a protective panel 8 which prohibits access to opening 10 until it is determined that access to the patient's femoral F artery is needed. In that case, panel 8 is lifted or removed and opening 10 is accessed. Also shown in FIG. 2 are adhesive rings 7 which will be described in greater detail later.

Located at one end of main sheet 4 are a plurality of sheet extension panels 11a and 11b. These adjustable arm board covers 11a and 11b include openings or fenestrations 14 and 18. Openings 14 and 18 can be utilized to access the patient's radial R and brachial B arteries, respectively, in each of the patient's arms A (FIG. 1). Positioned over openings 14 and 18 are protective panels 12 and 16, respectively, which prohibit access to openings 14 and 18 until it is determined that access to the patient's radial R and/or brachial B arteries is needed. In that case, panels 12 and/or 16 are lifted or removed and openings 14 and/or 18 are accessed. Also shown in FIG. 2 are adhesive rings 15 and 19 which will be described in greater detail later.

Adjustable arm board covers 11a and 11b are attached by a conventional adhesive to sheet folds 20. Sheet folds 20 are attached by a conventional adhesive to main sheet 4. In this manner, adjustable arm board covers 11a and 11b can be rotated or placed along the patient's arms A so that the patient's brachial B and radial R arteries can be easily accessed during the medical procedure, as will be discussed in greater detail later.

Figure 3:
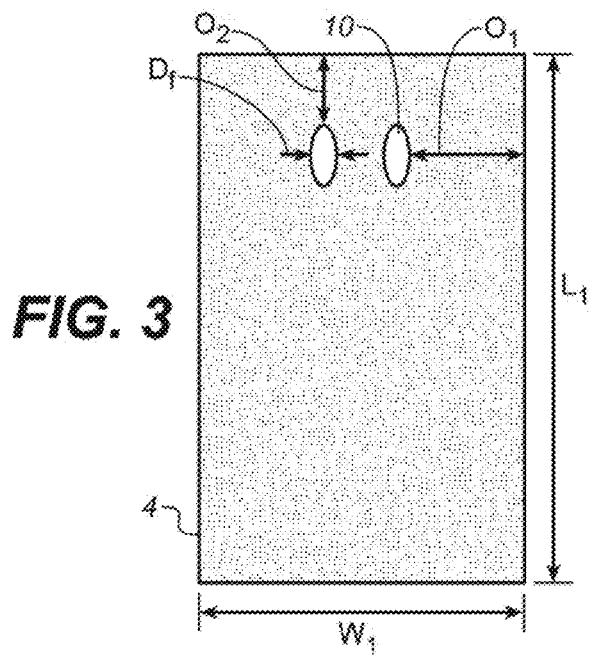
FIG. 3 is a top view of a leg section of the triple access drape, constructed according to the present invention.

As shown more clearly in FIG. 3, main sheet 4, preferably, is constructed of any suitable fire retardant, chemical resistant, and biodegradable material. Main sheet 4, preferably, has a width range $W_1$ of 81±2 cm and a length range $L_1$ of 319±5 cm. Openings 10, preferably, are located at a range $O_1$ of 24 cm from the side edge of main sheet 4 and at a range $O_2$ of 20 cm from the top of main sheet 4. Openings 10, preferably, are 15 cm wide, 11.5 cm in height, and 9 cm across its shorter axis $D_f$ (FIG. 1).

Figure 4:
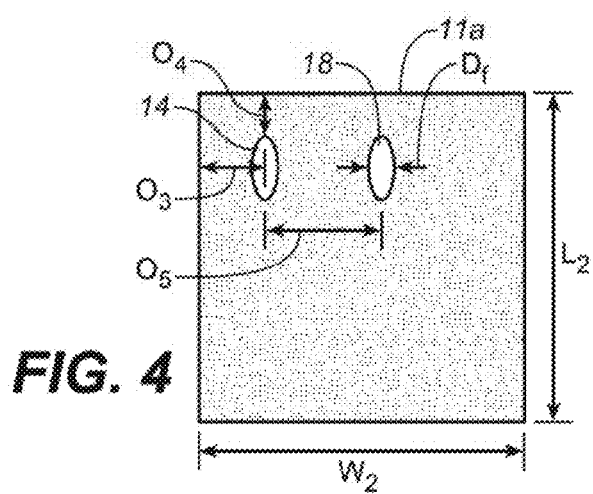
FIG. 4 is a top view of a right arm adjustable arm board cover of the triple access drape, constructed according to the present invention.

As shown more clearly in FIG. 4, right arm adjustable arm board cover 11a (FIG. 4), preferably, is constructed of any suitable fire retardant, chemical resistant, and biodegradable material. Right arm adjustable arm board cover 11a, preferably, has a width range $W_2$ of 96.5±2 cm and a length range $L_2$ of 80±2 cm. Opening 14, preferably, is located at a range $O_3$ of 14±2 cm from the side edge of right arm adjustable arm board cover 11a and at a range $O_4$ of 10±2 cm from the top of right arm adjustable arm board cover 11a. Opening 18, preferably, is located at a range $O_5$ of 14±2 cm from the center of opening 14. Openings 14 and 18, preferably, are 12.5 cm wide, 9 cm in height, and 6.5 cm across their shorter axes $D_f$.

Figure 5:
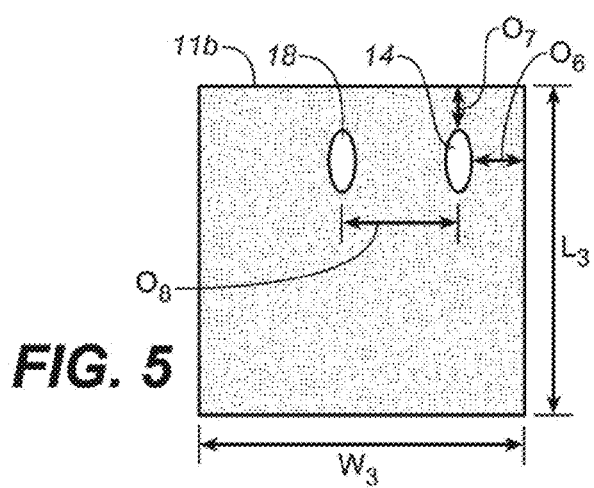
FIG. 5 is a top view of a left arm adjustable arm board cover of the triple access drape, constructed according to the present invention.

With respect to left arm adjustable arm board cover 11b, as shown more clearly in FIG. 5, left arm adjustable arm board cover 11b, preferably, is constructed of any suitable fire retardant, chemical resistant, and biodegradable material. Left arm adjustable arm board cover 11b, preferably, has a width range $W_3$ of 96.5±2 cm and a length range $L_3$ of 80±2 cm. Opening 14, preferably, is located at a range $O_6$ of 14±2 cm from the side edge of left arm adjustable arm board cover 11b and at a range $O_7$ of 10±2 cm from the top of left arm adjustable arm board cover 11b. Opening 18, preferably, is located at a range $O_8$ of 14±2 cm from the center of opening 14.

Figure 6:
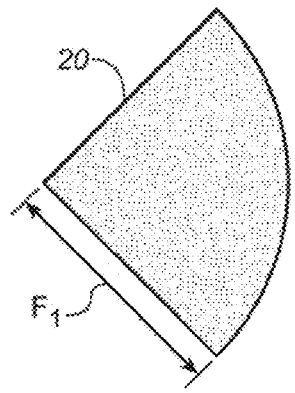
FIG. 6 is a top view of a fold section of the triple access drape, constructed according to the present invention.

With respect to FIG. 6, sheet folds 20 are illustrated. Sheet folds 20, preferably, are constructed of any suitable fire retardant, chemical resistant, and biodegradable material. Sheet folds 20, preferably, have a radius range $F_1$ of 40±3 cm.

With respect to panels 8 (FIG. 2), panels 8, preferably, are constructed of any suitable spunbond, meltblown, spunbond nonwoven (SMS) material that is fire retardant, chemical resistant, and biodegradable. Panels 8, preferably, have a width range of 18±1 cm and a length range of 18±1 cm. Panels 8, preferably, are attached to main sheet 4 at one end 9 of panel 8.

With respect to panels 12 and 16 (FIG. 2), panels 12 and 16, preferably, are constructed of any suitable spunbond, meltblown, spunbond nonwoven (SMS) material that is fire retardant, chemical resistant, and biodegradable. Panels 12 and 16, preferably, have a width range of 18±1 cm and a length range of 18±1 cm. Panels 12 and 16, preferably, are attached to adjustable arm board covers panels 11a and 11b at one end 13 and 17, respectively of adjustable arm board covers panels 11a and 11b.

Figure 7:
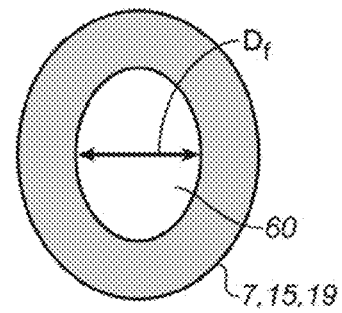
FIG. 7 is a top view of a fenestration reinforcement of the triple access drape, constructed according to the present invention.

As shown more clearly in FIG. 7, adhesive rings 7, are illustrated. Rings 7 are used to cover over openings 10, 14 and 18. Adhesive rings are constructed of any suitable adhesive incise adhesive. Adhesive rings 7, 15 and 17 are also used to attach triple access drape 2 to the patient, as will be described more completely later. Adhesive rings 7, preferably, are 15 cm wide, 11.5 cm in height and have a diameter $D_f$ of 9 cm. Adhesive rings 15 and 17 (FIG. 2) are 12.5 cm wide, 9 cm in height and have a diameter $D_f$ of 6.5 cm. It is to be understood that adhesive rings 15 and 17 are constructed of substantially the same material as adhesive ring 7.

A further important feature of the invention is illustrated in FIG. 7. An anesthesia window 60 is attached to the side of adhesive ring 7 such that anesthesia window 60 is substantially located between adhesive rings 7 and main sheet 4. Anesthesia window 60 is also located between adhesive rings 15 and 17 and adjustable arm board covers 11a and 11b. Once triple access drape 2 is placed over the patient, anesthesia window 60 will provide a clear view of the locations for accessing the patient's femoral F, brachial B and/or radial R arteries (FIG. 1). The medical personnel then merely have to insert the desired medical device through the anesthesia window 60 such that the medical device interacts with the patient's femoral F, brachial B and/or radial R arteries. In this manner, anesthesia window 60 protects the area around the patient's femoral F, brachial B and/or radial R arteries until such access is needed.

With respect to anesthesia window 60, a hole having the desired dimensions is simply cut in main sheet 4 or adjustable arm board covers 11a and 11b. Anesthesia window 60 is then placed over the hole in main sheet 4 or adjustable arm board covers 11a and 11b and conventionally attached to adhesive ring 7 to main sheet 4 or adjustable arm board covers 11a and 11b. Anesthesia window 60, preferably, is constructed of any suitable clear material such as clear polyethylene.

Figure 8:
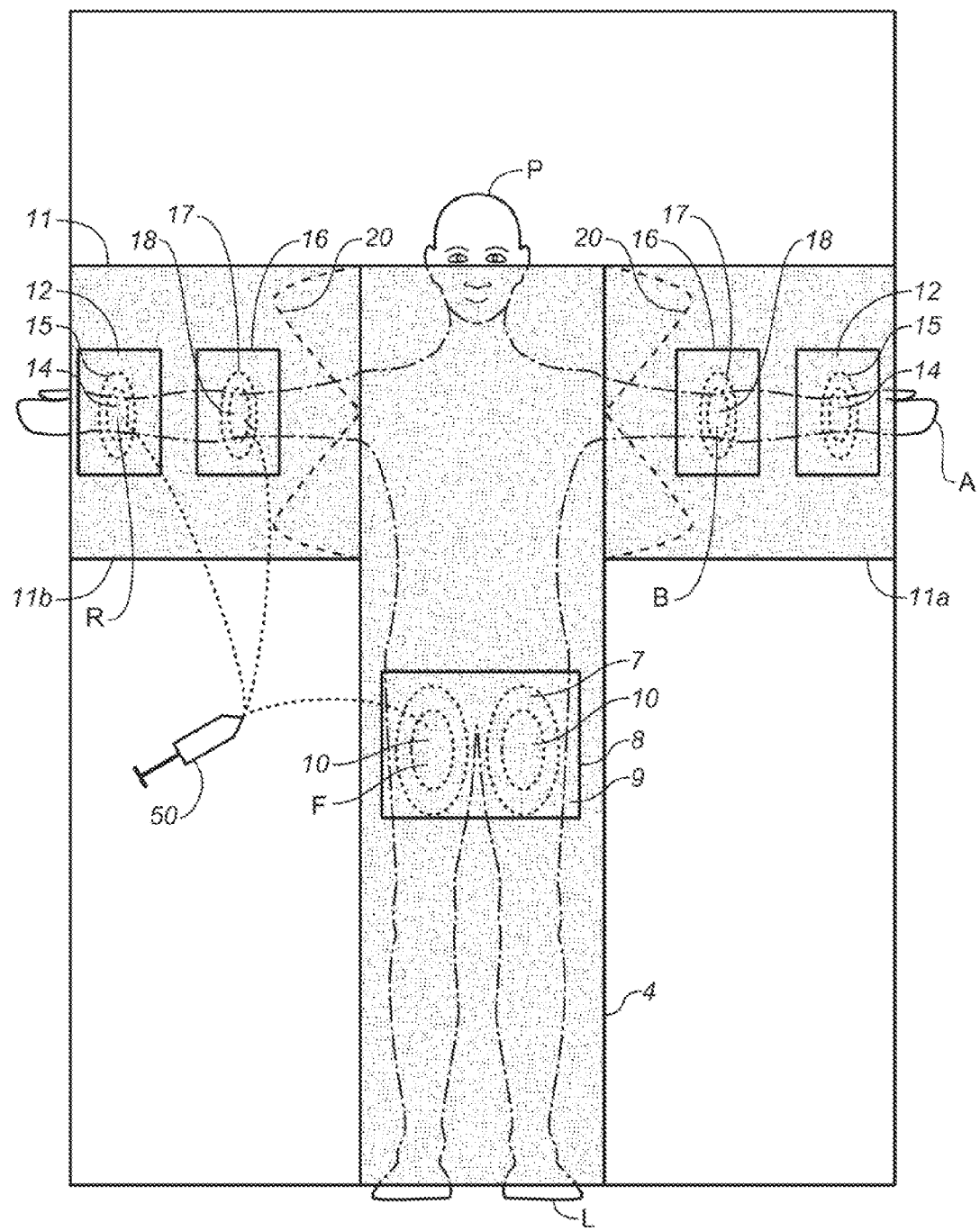
FIG. 8 is a top view of the triple access drape being located on a human body, in accordance with the present invention.

With respect to FIG. 8, there is illustrated another important feature of the present invention. In particular, FIG. 8 illustrates the placement of the triple access drape 2 over the patient P and the orienting of main sheet 4 and adjustable arm board covers 11a and 11b such that openings 10, 14 and 18 are located over the patient's femoral F, radial R, and brachial B arteries, respectively, and the securing of triple access drape 2 to the patient P at the femoral F, radial R and brachial B arteries, respectively by adhesive rings 7, 15 and 17, respectively. It is to be understood that prior to placing the triple access drape 2 over the patient, the patient's femoral F, radial R and brachial B arteries are conventionally marked on the patient's skin so that the triple access drape 2 can be properly located over the patient P.

Prior to the start of the medical procedure, for example, a surgical procedure, the patient P is placed upon an operating room table (not shown). According to one of the inventive aspects of the present invention, as shown more clearly in FIG. 8, the patient P is covered loosely with the triple access drape 2. The adjustable arm board covers 11a and 11b are adjusted so that the patient's brachial B and radial R arteries are properly located within openings 14 and 18, respectively. The patient's femoral F arteries are also properly located within openings 10 in main sheet 4. Once the patient's brachial B, radial R and femoral F arteries are properly located, adhesive rings 7, 15 and 17 are used to secure triple access drape 2 to the patient P at those locations only. The remainder of triple access drape 2 is allowed to lie loosely over the patient P.

After the triple access drape 2 is secured onto the patient P, the surgical personnel can access any or all of the brachial B, radial R and femoral F arteries by lifting up or removing the panels 16, 12 and/or 8, respectively and accessing the desired artery or arteries through anesthesia windows 60 such that conventional medical device 50 can be inserted to any or all of the brachial B, radial R and femoral F arteries.

Figure 9:
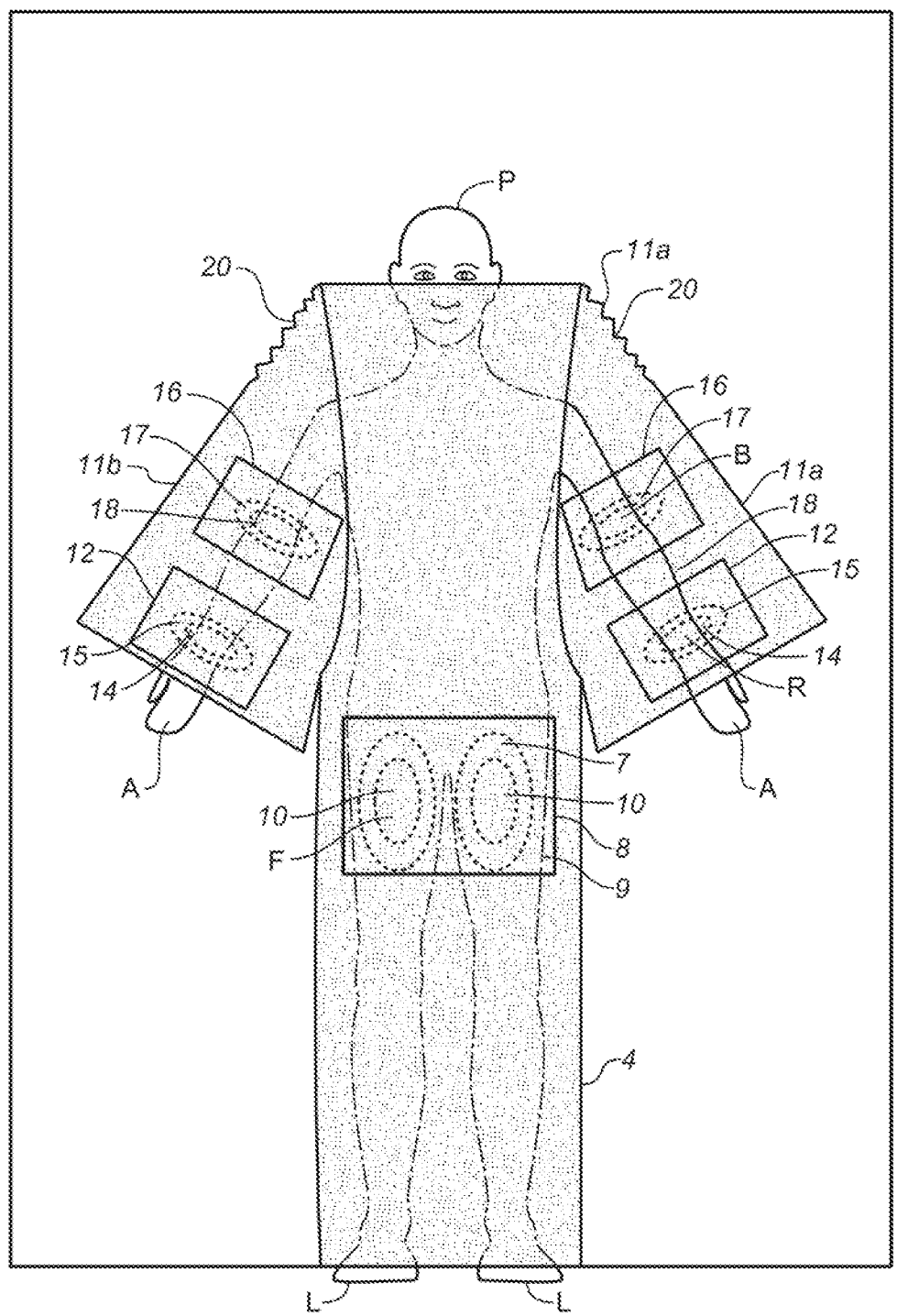
FIG. 9 is a top view of the triple access drape being located on a human body with the human's arms being located at the human's side, in accordance with the present invention.

With respect to FIG. 9, there is illustrated another inventive concept of the present invention. As shown more clearly in FIG. 9, the patient P is covered loosely with the triple access drape 2 while the patient's arms are located at the side of the patient. The adjustable arm board covers 11a and 11b are adjusted so that the patient's brachial B and radial R arteries are properly located within openings 14 and 18, respectively. The patient's femoral F arteries are also properly located within openings 10 in main sheet 4. As clearly shown in FIG. 9, adjustable arm board covers 11a and 11b create a hinged design that allow access to the patient's arms A and legs L regardless of the position of the patient's arms A and legs L. Once the patient's brachial B, radial R and femoral F arteries are properly located, adhesive rings 7, 15 and 17 are used to secure triple access drape 2 to the patient P at those locations only. The remainder of triple access drape 2 is allowed to lie loosely over the patient P.

As with the triple access drape shown in FIG. 8, after the triple access drape 2 of FIG. 9 is secured onto the patient P, the surgical personnel can access any or all of the brachial B, radial R and femoral F arteries by lifting up or removing the panels 16, 12 and/or 8, respectively and accessing the desired artery or arteries through anesthesia windows 60.

Figure 10:
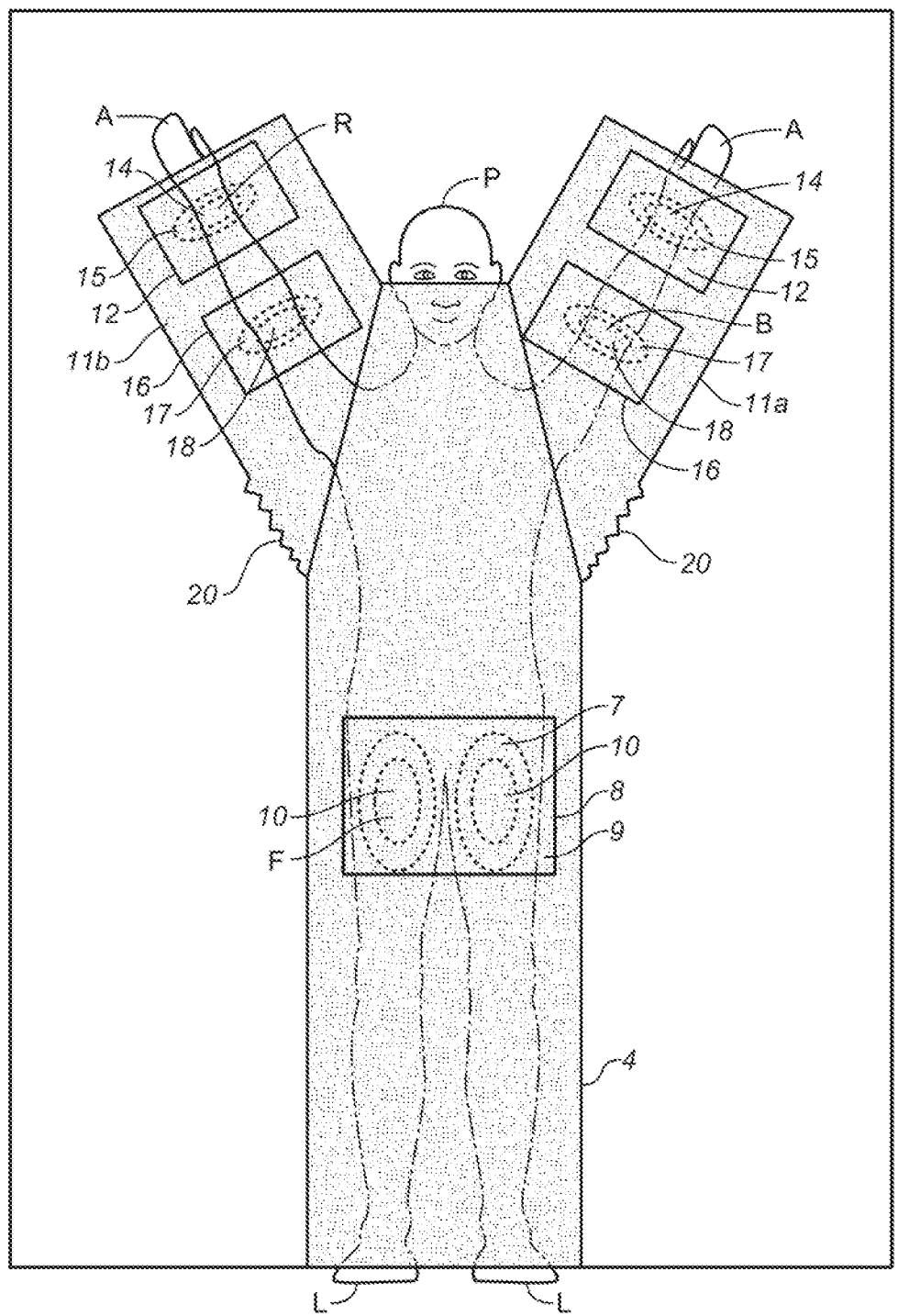
FIG. 10 is a top view of the triple access drape being located on a human body with the human's arms being located over the human's head, in accordance with the present invention

With respect to FIG. 10, there is illustrated still another inventive concept of the present invention. As shown more clearly in FIG. 10, the patient P is covered loosely with the triple access drape 2 while the patient's arms are located over the head of the patient. The adjustable arm board covers 11a and 11b are adjusted so that the patient's brachial B and radial R arteries are properly located within openings 14 and 18, respectively. The patient's femoral F arteries are also properly located within openings 10 in main sheet 4. As clearly shown in FIG. 10, adjustable arm board covers 11a and 11b create a hinged design that allow access to the patient's arms A and legs L regardless of the position of the patient's arms A and legs L. Once the patient's brachial B, radial R and femoral F arteries are properly located, adhesive rings 7, 15 and 17 are used to secure triple access drape 2 to the patient P at those locations only. The remainder of triple access drape 2 is allowed to lie loosely over the patient P.

As with the triple access drape shown in FIGS. 8 and 9, after the triple access drape 2 of FIG. 10 is secured onto the patient P, the surgical personnel can access any or all of the brachial B, radial R and femoral F arteries by lifting up or removing the panels 16, 12 and/or 8, respectively and accessing the desired artery or arteries through anesthesia windows 60.

The preceding merely illustrates the principles of the invention. It will thus be appreciated that those skilled in the art will be able to devise various arrangements which, although not explicitly described or shown herein, embody the principles of the invention and are included within its spirit and scope. Furthermore, all examples and conditional language recited herein are principally intended expressly to be only for pedagogical purposes and to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention, as well as specific examples thereof, are intended to encompass both structural and functional equivalents thereof. Additionally, it is intended that such equivalents include both currently known equivalents and equivalents developed in the future, i.e., any elements developed that perform the same function, regardless of structure.

This description of the exemplary embodiments is intended to be read in connection with the figures of the accompanying drawing, which are to be considered part of the entire written description. In the description, relative terms such as "lower," "upper," "horizontal," "vertical," "above," "below," "up," "down," "top" and "bottom" as well as derivatives thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

All patents, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Applicants reserve the right to physically incorporate into this specification any and all materials and information from any such patents, publications, scientific articles, web sites, electronically available information, and other referenced materials or documents to the extent such incorporated materials and information are not inconsistent with the description herein.

The written description portion of this patent includes all claims. Furthermore, all claims, including all original claims as well as all claims from any and all priority documents, are hereby incorporated by reference in their entirety into the written description portion of the specification, and Applicant(s) reserve the right to physically incorporate into the written description or any other portion of the application, any and all such claims. Thus, for example, under no circumstances may the patent be interpreted as allegedly not providing a written description for a claim on the assertion that the precise wording of the claim is not set forth in haec verba in written description portion of the patent.

The claims will be interpreted according to law. However, and notwithstanding the alleged or perceived ease or difficulty of interpreting any claim or portion thereof, under no circumstances may any adjustment or amendment of a claim or any portion thereof during prosecution of the application or applications leading to this patent be interpreted as having forfeited any right to any and all equivalents thereof that do not form a part of the prior art.

All of the features disclosed in this specification may be combined in any combination. Thus, unless expressly stated otherwise, each feature disclosed is only an example of a generic series of equivalent or similar features.

It is to be understood that while the invention has been described in conjunction with the detailed description thereof, the foregoing description is intended to illustrate and not limit the scope of the invention, which is defined by the scope of the appended claims. Thus, from the foregoing, it will be appreciated that, although specific embodiments of the invention have been described herein for the purpose of illustration, various modifications may be made without deviating from the spirit and scope of the invention. Other aspects, advantages, and modifications are within the scope of the following claims and the present invention is not limited except as by the appended claims.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, the terms "comprising", "including", "containing", etc. are to be read expansively and without limitation. The methods and processes illustratively described herein suitably may be practiced in differing orders of steps, and that they are not necessarily restricted to the orders of steps indicated herein or in the claims.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by various embodiments and/or preferred embodiments and optional features, any and all modifications and variations of the concepts herein disclosed that may be resorted to by those skilled in the art are considered to be within the scope of this invention as defined by the appended claims.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

It is also to be understood that as used herein and in the appended claims, the singular forms "a," "an," and "the" include plural reference unless the context clearly dictates otherwise, the term "X and/or Y" means "X" or "Y" or both "X" and "Y", and the letter "s" following a noun designates both the plural and singular forms of that noun. In addition, where features or aspects of the invention are described in terms of Markush groups, it is intended and those skilled in the art will recognize, that the invention embraces and is also thereby described in terms of any individual member or subgroup of members of the Markush group.

Other embodiments are within the following claims. Therefore, the patent may not be interpreted to be limited to the specific examples or embodiments or methods specifically and/or expressly disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

Although the invention has been described in terms of exemplary embodiments, it is not limited thereto. Rather, the appended claims should be construed broadly, to include other variants and embodiments of the invention, which may be made by those skilled in the art without departing from the scope and range of equivalents of the invention.

Other modifications and implementations will occur to those skilled in the art without departing from the spirit and the scope of the invention as claimed. Accordingly, the description hereinabove is not intended to limit the invention, except as indicated in the appended claims.

Therefore, provided herein are a new and improved triple access drape and a novel method of using the triple access drape. The preferred triple access drape, according to various embodiments of the present invention, offers the following advantages: ease of use; economy of design; the patient does not need to be re-draped in order to achieve access; and the adjustable arm board covers create a hinged design that allows access to the patient regardless of position.

I claim:

1. A medical drape, comprising:
   a main sheet having at least one opening for access to a patient's femoral artery, wherein the main sheet is further comprised of at least one adhesive ring located substantially to surround the at least one opening and wherein the adhesive ring is further comprised of an anesthesia window that is located substantially over the at least one opening for access to the patient's femoral artery; and
   at least one adjustable arm board cover substantially located at one end of the main sheet wherein the adjustable arm board cover includes at least one opening for access to the patient's brachial artery and at least one opening for access to the patient's radial artery, wherein the adjustable arm board cover is further comprised of at least one adhesive ring located substantially to surround the at least one opening for access to the patient's brachial artery and at least one adhesive ring located substantially to surround the at least one opening for access to the patient's radial artery and wherein the adhesive ring located substantially to surround the at least one opening for access to the patient's brachial artery is further comprised of an anesthesia window that is located substantially over the at least one opening for access to the patient's brachial artery and another anesthesia window that is located substantially over the at least one opening for access to the patient's radial artery.

2. The medical drape, as in claim 1, wherein the main sheet is further comprised of:
   a protective panel located substantially over the adhesive ring.

3. The medical drape, as in claim 2, wherein the protective panel is further comprised of:
   any suitable fire retardant, chemical resistant, and biodegradable spunbond, meltblown, spunbond nonwoven (SMS) material.

4. The medical drape, as in claim 1, wherein the medical drape is further comprised of:
   at least one drape fold operatively connected to the main sheet and the adjustable arm board cover.

5. The medical drape, as in claim 4, wherein the at least one drape fold is further comprised of: any suitable fire retardant, chemical resistant, and biodegradable material.

6. The medical drape, as in claim 1, wherein the main sheet is further comprised of:
   two openings.

7. The medical drape, as in claim 1, wherein the adjustable arm board cover is further comprised of:
   two openings.

8. The medical drape, as in claim 1, wherein the adjustable arm board cover is further comprised of:
   a protective panel located substantially over the at least one adhesive ring located substantially over the at least one opening for access to the patient's brachial artery and a protective panel located substantially over the at least one adhesive ring located substantially over the at least one opening for access to the patient's radial artery.

9. The medical drape, as in claim 1, wherein the main sheet and the adjustable arm board cover are further comprised of:
   any suitable fire retardant, chemical resistant, and biodegradable material.

10. The medical drape, as in claim 1, wherein the adhesive ring is further comprised of:
    any suitable adhesive incise material.

11. The medical drape, as in claim 1, wherein the anesthesia window is further comprised of:
 clear polyethylene.

12. A method of attaching a triple access drape to a patient, wherein the method is comprised of the steps of:
 placing the triple access drape substantially over the patient, wherein the triple access drape includes a main sheet having at least one opening for access to a patient's femoral artery, wherein the main sheet is further comprised of at least one adhesive ring located substantially to surround the at least one opening and wherein the adhesive ring is further comprised of an anesthesia window that is located substantially over the at least one opening for access to the patient's femoral artery; and at least one adjustable arm board cover substantially located at one end of the main sheet wherein the adjustable arm board cover includes at least one opening for access to the patient's brachial artery and at least one opening for access to the patient's radial artery, wherein the adjustable arm board cover is further comprised of at least one adhesive ring located substantially to surround the at least one opening for access to the patient's brachial artery and at least one adhesive ring located substantially to surround the at least one opening for access to the patient's radial artery and wherein the adhesive ring located substantially to surround the at least one opening for access to the patient's brachial artery is further comprised of an anesthesia window that is located substantially over the at least one opening for access to the patient's brachial artery and another anesthesia window that is located substantially over the at least one opening for access to the patient's radial artery;
 locating the at least one opening for access to a patient's femoral artery substantially over the patient's femoral artery;
 locating the at least one opening for access to the patient's brachial artery substantially over the patient's brachial artery;
 locating the at least one opening for access to the patient's radial artery substantially over the patient's radial artery; and
 securing the triple access drape at the at least one openings for access to a patient's femoral artery, brachial artery and radial artery.

13. The method, as in claim 12, wherein the method is further comprised of the step of:
 lifting a protective panel located substantially over each of the at least one openings for access to the patient's femoral, brachial, and radial arteries to access the patient's femoral, brachial, and radial arteries.

14. The method, as in claim 13, wherein the method is further comprised of the step of:
 inserting a medical device substantially through the anesthesia window located substantially under each of the protective panels.

15. The method, as in claim 12, wherein the method is further comprised of the step of:
 using an adhesive ring to secure the triple access drape to the patient.

16. A medical drape, comprising:
 a longitudinal sheet having a sufficient longitudinal length to drape a torso of a patient from neck to ankles, said longitudinal sheet having at least one femoral artery access opening for providing femoral artery access without repositioning a draped patient or said longitudinal sheet during a surgical procedure;
 a pair of lateral adjustable arm board covers, each individual arm board cover having a sufficient lateral length to drape a patient from shoulder to about a lower arm midpoint area, wherein one of said pair of lateral adjustable arm board covers has at least one radial artery access opening for providing radial artery access of the draped patient during a surgical procedure, and wherein another one of said pair of lateral adjustable arm board covers has at least one brachial artery access opening for providing brachial artery access of the draped patent during the surgical procedure;
 a set of adhesive rings, each individual adhesive ring having an anesthesia window secured to one side thereof for enabling medical personnel to see a marked artery location on a patient and for keeping a area about the marked artery location sterile until access to the artery is necessary during the surgical procedure, and a sufficient adhesive surface on another side thereof to adhesively secure said longitudinal sheet and said pair of lateral adjustable arm board respectively only at about a marked femoral artery location and at about a marked radial artery location and at about a marked brachial artery location of the patient; and
 a set of removable protective panels for covering said set of adhesive rings, each individual panel being removable from the medical drape to substantially avoid repositioning of the medical drape or the patient when access to one or more of the femoral arteries, radial arteries or brachial arteries is necessary during the surgical procedure.

17. The medical drape according to claim 16, wherein each individual one of said pair of lateral adjustable arm board covers is hinged to allow access to the arms of a patient regardless of arm positioning prior to a surgical procedure.

18. A medical drape, comprising:
 a main sheet having at least one opening for access to a patient's femoral artery, wherein the main sheet is further comprised of at least one adhesive ring located substantially to surround the at least one opening and wherein the adhesive ring is further comprised of an anesthesia window that is located substantially over the at least one opening for access to the patient's femoral artery;
 at least one adjustable arm board cover substantially located at one end of the main sheet wherein the adjustable arm board cover includes at least one opening for access to the patient's brachial artery and at least one opening for access to the patient's radial artery, wherein the adjustable arm board cover is further comprised of at least one adhesive ring located substantially to surround the at least one opening for access to the patient's brachial artery and at least one adhesive ring located substantially to surround the at least one opening for access to the patient's radial artery and wherein the adhesive ring located substantially to surround the at least one opening for access to the patient's brachial artery is further comprised of an anesthesia window that is located substantially over the at least one opening for access to the patient's brachial artery and another anesthesia window that is located substantially over the at least one opening for access to the patient's radial artery; and
 at least one drape fold operatively connected to the main sheet and the adjustable arm board cover.

* * * * *